US006407809B1

(12) United States Patent
Finarov et al.

(10) Patent No.: US 6,407,809 B1
(45) Date of Patent: Jun. 18, 2002

(54) OPTICAL INSPECTION SYSTEM AND METHOD

(75) Inventors: Moshe Finarov, Rehovot; Natalie Levinsohn, Hadera; Shay Ghilai, Tel-Aviv, all of (IL)

(73) Assignee: Nova Measuring Instruments Ltd., Rehovot (IL)

( * ) Notice: Subject to any disclaimer, the term of this patent is extended or adjusted under 35 U.S.C. 154(b) by 0 days.

(21) Appl. No.: 09/501,230

(22) Filed: Feb. 10, 2000

(30) Foreign Application Priority Data

May 24, 1999 (IL) .................................................. 130087

(51) Int. Cl.[7] ............................................. G01N 21/00
(52) U.S. Cl. ................................. 356/237.3; 356/237.4
(58) Field of Search ........................... 356/237.1, 237.3, 356/237.2, 237.5, 237.6, 239.7, 239.8; 250/559.45, 559.46, 559.47, 559.48, 559.49

(56) References Cited

U.S. PATENT DOCUMENTS

| 4,630,276 | A | | 12/1986 | Moran |
| 5,108,176 | A | | 4/1992 | Malin et al. |
| 5,127,726 | A | | 7/1992 | Moran |
| 5,274,434 | A | | 12/1993 | Morioka et al. |
| 5,298,989 | A | * | 3/1994 | Tsukahara et al. .......... 348/126 |
| 5,644,393 | A | | 7/1997 | Nakamura et al. |
| 5,712,701 | A | | 1/1998 | Clementi et al. |
| 5,768,443 | A | | 6/1998 | Michael et al. |
| 6,020,957 | A | | 2/2000 | Rosengaus et al. |

FOREIGN PATENT DOCUMENTS

EP 0 466 838 9/1991

* cited by examiner

Primary Examiner—Hoa Q. Pham
(74) Attorney, Agent, or Firm—Browdy and Neimark

(57) ABSTRACT

An optical inspection system is presented, aimed at detecting defects on a substantially flat workpiece having an axis of symmetry. The workpiece is supported on a stage so as to be in an inspection plane, the stage being mounted for rotation in a plane parallel to the inspection plane. A scanning apparatus is accommodated above the workpiece, and comprises an illumination assembly, a plurality of optical assemblies, and a plurality of area sensors. The illumination assembly produces a plurality of incident radiation components for illuminating a strip on the workpiece extending parallel to the axis symmetry between two opposite sides thereof. The optical assemblies are aligned along the axis of symmetry in a spaced-apart parallel relationship, and are mounted for reciprocating movement within a plane parallel to an inspection area that covers substantially a half of the workpiece. The area sensors are arranged in a predetermined manner, each area sensor being associated with a corresponding one of the optical assemblies for receiving a component of returned radiation and generating data representative thereof. The half of the workpiece is strip-by-strip inspected, then the stage with the workpiece is rotated by 180° and the other half of the workpiece is strip-by-strip inspected.

28 Claims, 9 Drawing Sheets

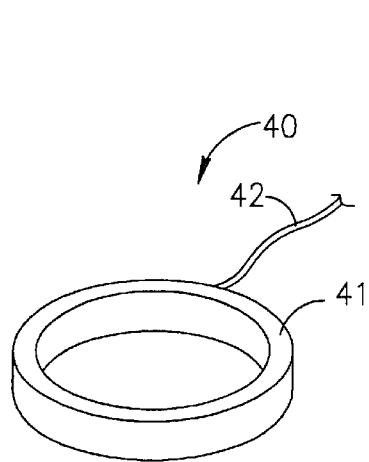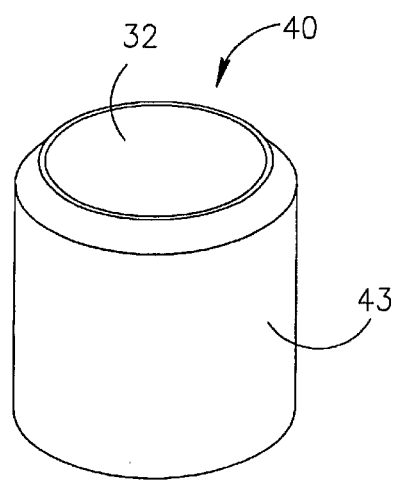
FIG.4A　　　　　　FIG.4B
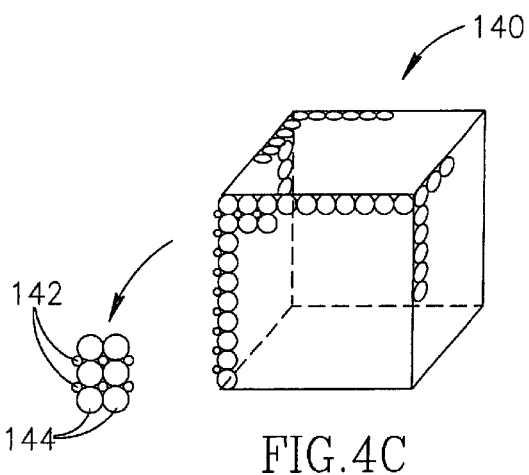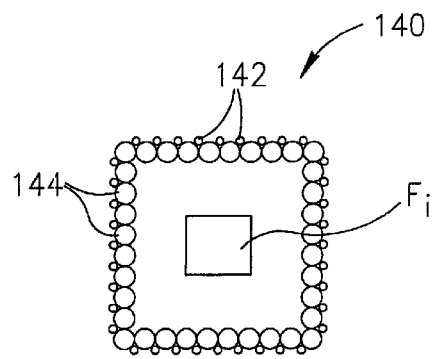
FIG.4C　　　　　　FIG.4D
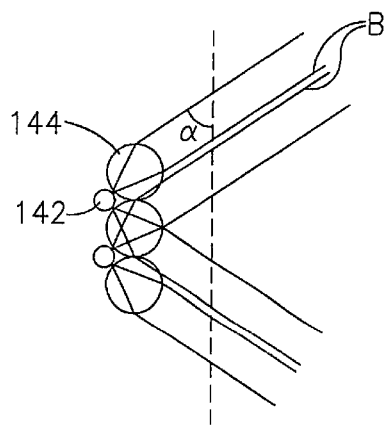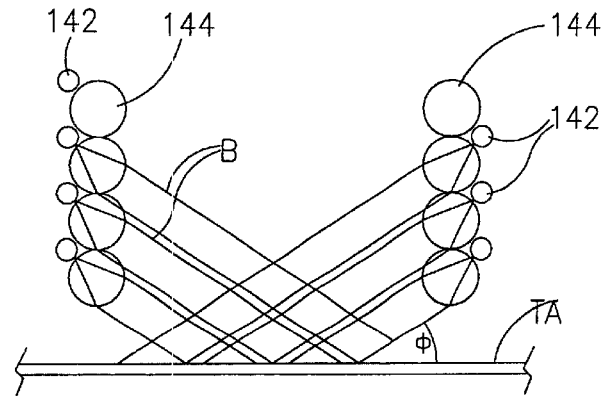
FIG.4E　　　　　　FIG.4F

OPTICAL INSPECTION SYSTEM AND METHOD

FIELD OF THE INVENTION

The present invention is in the field of automatic inspection techniques, and relates to an optical inspection method and system, particularly useful for inspecting semiconductor wafers progressing on a production line.

BACKGROUND OF THE INVENTION

The manufacture of semiconductor devices consists of a multi-staged process requiring wafers progressing on a production line to be inspected between sequential manufacturing steps. One of the principle processes in the manufacture of semiconductor devices is the photolithography process. It consists of patterning the wafer's surface in accordance with the active elements of semiconductor devices to be manufactured. The photolithography process includes the following main operational steps:

a. Coating the wafer with a photoresist material;

b. Exposing the photoresist material through a mask with a predetermined pattern in order to produce a latent image of the mask on the photoresist material; and c. Developing the exposed photoresist material in order to produce the image of the mask on the wafer.

Generally speaking, prior to the photolithography process, the wafer is prepared for the deposition of one or more layers. After the completion of the photolithography process, the uppermost layer of the wafer is etched. Then a new layer is deposited, in order to start the photolithography and etching operations again. In this repetitive manner, a multi-layer semiconductor wafer is produced.

FIG. 1 illustrates a block diagram of a typical photocluster 1 used for performing the photolithography process in semiconductor fabrication plants (FABs). The photocluster 1 (or link) is composed of two main parts: a phototrack 2 and an exposure tool 4. The phototrack 2 includes a coater track 6 associated with a cassette load station 6a, and a developer back 8 associated with a cassette unload station 8a. Alternatively, both coating and developing functions may be combined and realized in a common station. A load/unload robot R is mounted for movement within the photocluster 1 for conveying wafers W to and from the photocluster tools. The coater track 6, the exposure tool 4 and the development track 8 are tightly joined together in order to minimize process variability and any potential risk of contamination during photolithography, which is a super sensitive process.

It is apparent that in such a complex and delicate production process various problems, failures or defects may arise or develop during each manufacturing step or from the serial combination of steps. Due to the stringent quality requirements, any defect which is not timely detected, may result in the rejection of a single wafer or the entire lot. The wafer cannot be taken out of tie photocluster tools set-up for measurement or inspection before the entire photolithography process is completed and the wafer arrives at the cassette station 8a. The wafers are typically inspected at a stand-alone monitoring system (CD-SEAM) which is installed outside the production line, and to which the wafers are transferred by means of a separate handling system. This reduces the throughput of the production line.

A manual inspection technique is conventionally used for inspecting the wafers for so-called macro lithography defects, such as scratches or foreign particles of dust and dirt. Generally, macro defects are considered as defects having tenths of micrometers in size. The manual inspection technique utilizes the visual examination of the wafers surface by an operator using intense light and magnification. This inspection is inconsistent and unreliable, since the results vary significantly amongst operators, due to the wafer's complexity and depending on the operators' experience. About 80% of the photo-related defects remain undetected. Manual inspection has low throughput, and could not be performed within the FAB tools. Manual inspection is not cost effective.

Various automatic inspection systems have been developed. They utilize either a line CCD camera or an area CCD camera The basic problem with line type detectors is their non-effective use of illuminating radiation. This is owing to the fact that a strip illuminated on the surface of the wafer under inspection is substantially wider than the width of the field of view of a line CCD camera. Additionally, the line CCD based technique suffers from a complicated mechanical arrangement needed for moving the line CCD camera along the X- and Y-axes relative to the wafer under inspection. Moreover, different resolutions are achieved in the X- and Y-directions, due to the movement of the image during scanning.

As for the area sensor based technique, it utilizes a so-called step-and-repeat mode of operation, wherein the camera and the wafer are mounted for movement relative to each other to cover the entire surface of the wafer. More specifically, the camera and the wafer are moved step-by-step, and images are acquired upon the camera or the wafer stops. The technique requires a quite complicated mechanical stage providing movement along two mutually perpendicular axes. Additionally, it results in low throughput due to a great number of movement steps, and requires an additional footprint for performing such a two-dimensional movement.

Machine vision systems having multiple cameras have been developed, being disclosed, for example, in U.S. Pat. No. 5,768,443. In this system, images are acquired simultaneously by a plurality of cameras. The fields of view of the cameras cover a relatively large area of the wafer under inspection, thereby increasing the throughput of the system, as compared to the techniques utilizing a single line or area sensor. However, this patent does not present any example of the cameras' arrangement, which would be useful in an integrated inspection. An inspection machine should be inexpensive, simple to erect and maintain, and should have a small footprint (like a wafer cassette) to meet the requirements of the integrated inspection.

Laser inspection systems have been developed which utilize various types of scanners and collectors for scanning the wafer's surface during the translational movement, and for collecting light reflective and scattered from the surface. Such systems are disclosed, for example, in U.S. Pat. Nos. 4,630,276; 5,108,176; 5,127,726 and 5,712,701. Unfortunately, these systems are complicated and expensive. Since they use monochromatic laser illumination, they are non-effective and insufficient for the inspection of developed photoresist for macro defects.

SUMMARY OF THE INVENTION

There is accordingly a need to facilitate the automatic inspection of workpieces progressing on a production line, by providing a novel system and method for the optical inspection of such workpieces.

It is a major feature of the invention that the optical inspection system may be integrated into the production line. It is simple, inexpensive and compact, and provides for inspection with a high throughput of workpieces.

The main idea of the present invention is based on the following. A semiconductor wafer is typically a substantially flat workpiece, having an axis of symmetry (i.e. is round). Consequentially, one half of the wafer can be inspected by appropriately moving respective parts of a scanning apparatus above it, and, upon rotating the wafer about its axis of symmetry by 180°, inspecting the other half of the wafer. Hence, suitable mechanics should be provided for moving the respective components of the scanning apparatus solely within an inspection area equal to the half of the wafer, rather than moving them above the entire wafer, or moving both the respective components and the wafer relative to each other. This significantly simplifies the mechanical equipment of the entire system, as well as its footprint, and enables the use of a robot typically installed in the production line for conveying wafers to and from a plurality of stations. To scan the half of the wafer (inspection area), a plurality of optical assemblies is mounted for movement above the wafer within the inspection area, the optical assemblies being aligned in a line parallel to the axis of symmetry of the wafer between the opposite sides thereof. A plurality of sensors is provided, each sensor being associated with a corresponding one of the plurality of optical assemblies. Thus, an illuminated strip extending along the entire width of the wafer is inspected at each location of the plurality of optical assemblies relative to the wafer.

There is thus provided, according to one aspect of the present invention, an optical inspection system for detecting defects on a substantially flat workpiece having an axis of symmetry, the system comprising a stage supporting said workpiece in an inspection plane, and a scanning apparatus accommodated above said workpiece, wherein:

(a) said stage is mounted for rotation in a plane parallel to said inspection plane;

(b) said scanning apparatus comprises:
   an illumination assembly producing a plurality of incident radiation components, each component illuminating a corresponding one of a plurality of regions of the workpiece within a strip illuminated by said plurality of incident radiation components, the strip extending parallel to the axis of symmetry of the workpiece between two opposite sides thereof;
   a plurality of optical assemblies accommodated above said workpiece, each optical assembly directing a corresponding one of a plurality of radiation components returned from the corresponding illuminated region away from the workpiece, wherein the optical assemblies are aligned along said axis of symmetry in a spaced-apart parallel relationship and mounted for reciprocating movement within a plane parallel to an inspection area, said inspection area covering substantially a half of the work-piece;

(c) a plurality of area sensors are arranged im a predetermined manner, each area sensor being associated with a corresponding one of the optical assemblies for receiving the component of the retained radiation and generating data representative thereof;

(d) a first drive mechanism is coupled to said optical assemblies for driving said reciprocating movement thereof; and (e) a second drive mechanism is coupled to said stage for driving said rotation thereof.

The illumination assembly may operate in bright-field illumination mode. In this case, it comprises a plurality of stationary mounted light sources aligned corresponding to the alignment of the optical assemblies, each incident radiation component being directed on the corresponding optical assembly, which, in turn, directs it onto the corresponding region of the workpiece.

Alternatively, or additionally, the illumination assembly may operate in a dark-filed illumination mode. In this case, it includes either a plurality of light sources, each accommodated in the vicinity of the corresponding optical assembly, or an elongated light source, extending along the optical assemblies in the proximity thereof. This "dark-field" illumination assembly is mounted for movement together with the optical assemblies If the dark-field light illumination is used in addition to the bright-field illumination, the operation of the stationary mounted light sources and the operation of the movable light sources are time separated. For example, the stationary mounted light sources may be continuously operated, while the movable light sources are selectively actuated to inspect only those locations on the workpiece where either a potential defect has been detected during the bright-field mode, or a real defect is expected.

The area sensors may be arranged in a line parallel to the axis of symmetry and associated with the optical assemblies, so as to move together with the optical assemblies. Alternatively, the area sensors may be arranged in two parallel lies, parallel to the axis of symmetry, wherein each two adjacent sensors are displaced from each other along two mutually perpendicular axes. In this case, an additional light directing assembly is provided for receiving the components of the returned radiation ensuing from the optical assemblies, and directing them onto to the area sensors.

According to another aspect of the present invention, there is provided a photolithography tool for processing a stream of substantial flat workpieces progressing on a production line, which tool comprises an optical inspection system constructed as described above.

According to yet another aspect of the present invention, there is provided a method for inspecting a substantial flat workpiece having an axis of symmetry, the method comprising the steps of:

(i) locating the workpiece within an inspection plane;

(j) illuminating a plurality of regions of the workpiece by a plurality of incident radiation components and producing a plurality of light components returned from the plurality of illuminated regions, the illuminated regions forming an illuminated strip extending parallel to the axis of symmetry between two opposite sides of the workpiece;

(k) directing each of the plurality of light components returned from the illuminated regions through a plurality of optical assemblies aligned in a line parallel to the axis of symmetry above the workpiece;

(l) detecting light components returned from the illuminated regions by a corresponding plurality of area sensors;

(m) moving said plurality of optical assemblies relative to said workpiece within a plane parallel to the inspection planes such as to illuminate successive strips on the workpiece and detect light components returned therefrom;

(n) repeating steps (j) to (n) for skip-by-strip inspection of the workpiece within an inspection area that covers substantially a half of the workpiece;

(o) rotating said workpiece by 180° and repeating steps (j) to (o).

More specifically, the present invention is used for inspecting wafers progressing within a photolithography tools set-up, and is therefore described below with respect to this application.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIGS. 4a and 4b illustrate two possible examples of implementation of au illumination assembly of the system of FIG. 3 operating in a dark-field illumination mode;

FIGS. 4c to 4f illustrate another possible example of a dark-field illumination assembly;

DETAILED DESCRIPTION OF A PREFERRED EMBODIMENT

Figure 1:
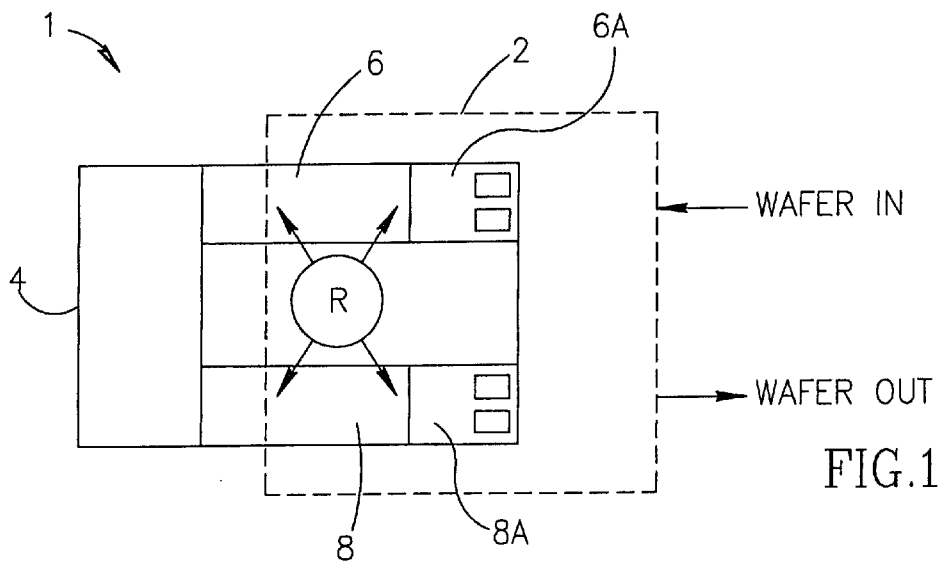
FIG. 1 schematically illustrates a block diagram of the main components of the conventional photocluster.

FIG. 1 illustrates the configuration of the conventional photocluster 1, which comprises the phototrack 2 and the exposure tool 4, wherein the photo track is composed of the coater track 6 and the developer track 8. The coater and developer tracks have their associated cassette load and unload stations 6a and 8a, respectively. The cassettes containing wafers are supplied to the phototrack 2, being loaded from the station 6a onto the coater track 6. Here, a photoresist material is deposited onto the wafer's surface, and then the robot R transmits the coated wafer to the exposure tool 4. The photoresist coating is exposed to light through a mask having a predetermined pattern to produce a latent image of the mask on the photoresist coating. Thereafter, the robot R transmits the wafer to the developer track 8 for developing the latent image.

Figure 2A:
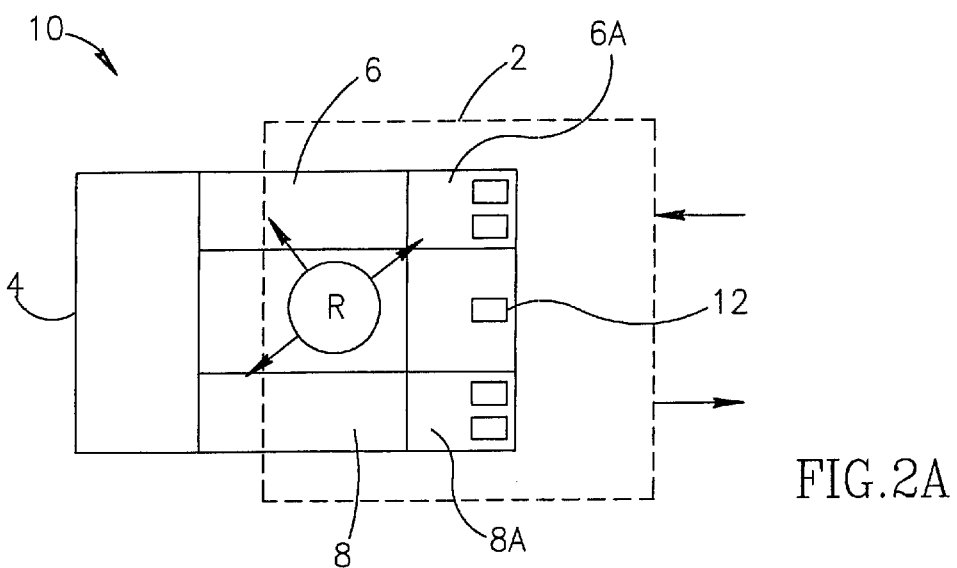
FIGS. 2a and 2b schematically illustrate by way of a block diagram two different examples, respectively, of a photolithography arrangement, including an optical inspection system according to the present invention.

Referring to FIG. 2a, there is illustrated a photocluster 10 (constituting a photolithography arrangement) constructed according to one example of the invention. The same reference numbers are used for identifying those components which are common in the photoclusters 1 and 10, to facilitate understanding. As shown, the photocluster 10 is constructed generally similar to the conventional photocluster 1, but comprises an optical inspection system 12, constructed and operated according to the invention, as will be described fiber below. The optical inspection system 12 is compact so as to be easily installed within the conventionally designed photocluster, enabling the use of the same robot R for feeding and discharging the wafers to and from the inspection system 12. The system 12 may be dimensioned and shaped similar to that of the conventional cassette. Generally, the exact location of the inspection system 12 within the photocluster is selected in accordance with the considerations and circumstances of a specific manufacturer, an available foot-print inside the phototrack and the FAD considerations. Since the inspection system 12 is extremely compact, it can be positioned at a cassette location in the unloading area, or any other location accessible for the load/unload robot R.

Figure 2B:
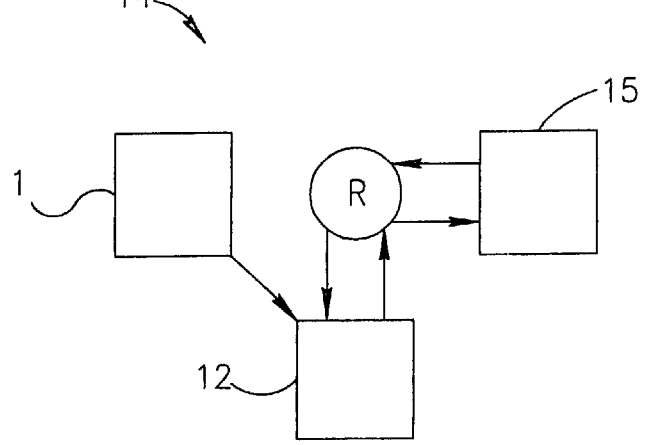

FIG. 2b illustrates a photolithography arrangement 14, constructed according to another example of the invention. The arrangement 14 utilizes the photocluster 1 and the optical inspection system 12, which is installed as a stand-alone unit within the photolithography arrangement 14 similar to the wafers' load/unload cassette station 15. The robot R conveys wafers from tie cassette 15 to the inspection system 12 and returns the inspected wafers back to the cassette station 15, and supplies and discharges wafers to and from the photocluster 1.

Figure 3A:
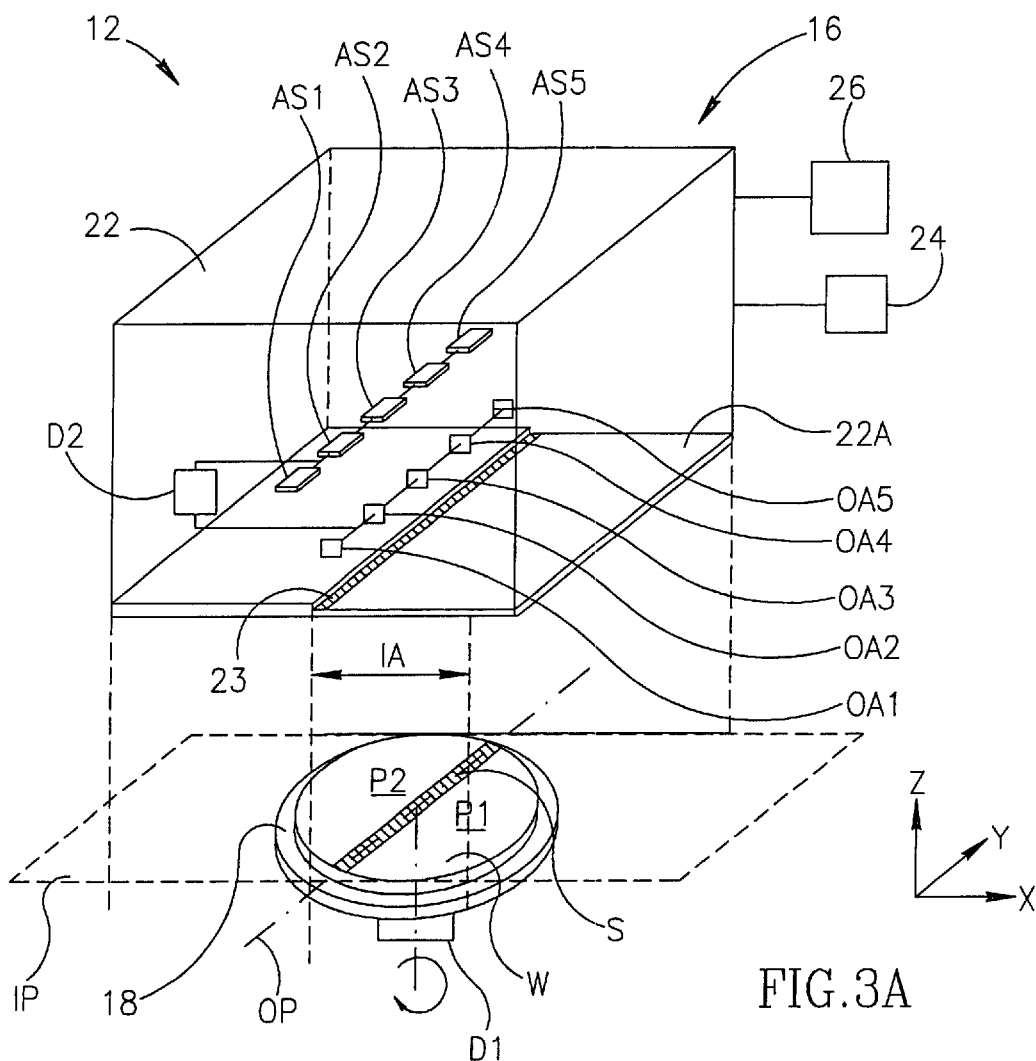
FIGS. 3a and 3b schematically illustrate the main components of the optical inspection system of either of FIGS. 2a or 2b, constructed according to one embodiment of the invention.

FIG. 3a illustrates the main constructional parts of the optical inspection system 12, constructed according to one embodiment of the invention. The inspection system 12 comprises a scanning apparatus 16 for inspecting a wafer W located on a support stage 18, which supports the wafer W in an inspection plane IP. The wafer W has an axis of its symmetry OP defining half-parts $P_1$ and $P_2$ of the wafer W at opposite sides of the axis OP. Coupled to the stage 18 is a first drive mechanism $D_1$ for driving the rotational movement of the stage 18 within a plane parallel to the inspection plane IP.

The scanning apparatus 16 inspects the wafer W wit an inspection area IA defined by the half $P_1$ of the wafer, as will be described more specifically further below. Then, the drive mechanism $D_1$ operates to rotate the stage 18 by 180°, thereby locating the other half $P_2$ of the wafer within the inspection area IA.

The scanning apparatus 16 comprises a sealed housing 22 containing a plurality of optical assemblies, for example five optical assemblies $OA_1$–$OA_5$, and a corresponding plurality of area sensors $AS_1$–$AS_5$. An illumination assembly 24 and a control unit 26 are accommodated outside the housing 22. The housing 22 is formed with an optically transparent bottom portion 22a (i.e., window) substantially covering the inspection area IA (one half of the wafer). A second drive mechanism $D_2$ is accommodated inside the housing so as to be outside the inspection area IA. The drive mechanism $D_2$ is associated with the optical assemblies $OA_1$–$OA_5$ and with the area sensors $AS_{1-AS5}$ for driving a reciprocation movement thereof along the X-axis within the inspection area IA. It is understood, although not specifically shown, that a suitable guiding assembly is provided for slidingly supporting the moving parts (i.e., optical assemblies and area sensors) to inside the housing 22.

The optical assemblies $OA_1$-$OA_5$ are accommodated above the window 22a being aligned along the Y-axis parallel to the axis of symmetry OP in a spaced-apart parallel relationship between the opposite sides of the wafer. The sensors $AS_1$–$AS_5$ are arranged like a "rule" extending along the Y-axis and spaced from the optical assemblies along the Z-axis.

The construction and operation of the control unit 26 do not form part of the present invention and may be of any known suitable kind, and therefore need not be specifically described, except to note the following The control unit 26 includes several suitable utilities. Some of them are associated with the sensors $AS_1$–$AS_5$ for receiving and analyzing data representative of radiation returned from the wafer W, and the other are associated with the driver assemblies $D_1$ and $D_2$ for synchronizing the movements of the stage 16 and moving components of the scanning apparatus. The control unit 26 is typically a computer device comprising a suitable pattern recognition software and a translation means so as to be responsive to data representative of the radiation returned from the wafer W and locate defect, if any. This software generates a gray level bit map of the acquired images, which may, for example, be stored in a memory. Generally speaking, the analyzing of the obtained data is performed in a die-to-die, die-to-many dies or die-to-database manner. The control unit 26 and the illumination assembly 24 are located outside the area occupied by the photocluster 1.

It should be noted 1 hat to facilitate the image processing, pre-alignment of the wafer W could be provided. When the wafer W is set on to the stage 18, the control unit 26 may operate the driver assemble $D_1$ to rotate the wafer W, and operate the periphery sensors, e.g. $AS_1$ and $AS_5$, along with the corresponding illuminating assemblies, to acquire images of the wafer's edge and analyze them, so as to detect a registration mark, i.e., "notch" or "flat". After the notch or flat is detected, the wafer could be turned so as to provide desired orientation of the main wafer direction. Preferably, the main wafer direction coincides with the X-axis, i.e., with the direction of movement of the optical assemblies $OA_1$–$OA_5$.

Figure 3B:
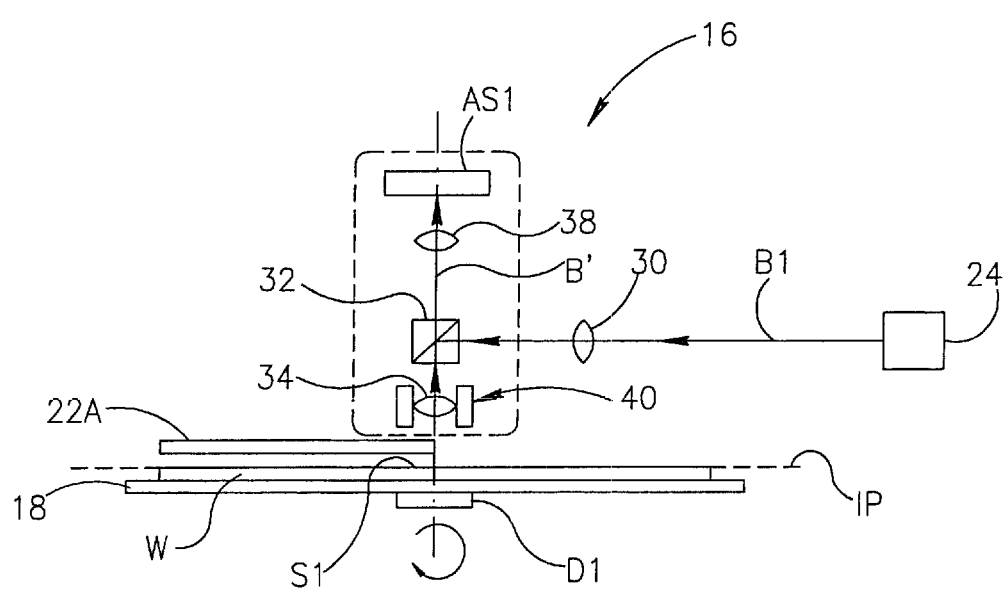

FIG. 3b schematically illustrates the main operational principles of the system 12. The beam propagation is shown here schematically to facilitate the illustration. The illumination assembly 24 comprises a suitable number of light sources or a single light source equipped with suitable light splitting means, capable of producing a plurality of incident light components. A corresponding number of lenses 30 are stationary mounted inside the housing 22 being aligned according to that of the optical assemblies. Each incident light component images onto a corresponding one of the optical assemblies (five in the present example), the component B, associated with the optical assembly $OA_1$ being seen in FIG. 3b. The optical assembly $OA_1$ comprises a beam splitter 32 and an objective lens assembly including inter alia a field lens 34. The area sensor $AS_1$ is associated with an imaging tube lens 38.

The beam splitter 32 directs the incident light component $B_1$ onto the objective lens assembly (only the field lens 34 thereof being shown here), which, in turn, focuses the light component $B_1$ onto a region $S_1$ on the wafer. A light component $B_1'$ returned from the illuminated region $S_1$ is directed onto the lens 38 by the beam splitter 32. It is understood, although not specifically shown, that regions illuminated by all the incident light components via the optical assemblies $OA_1$–$OA_5$ form together the illuminated strip S extending parallel to the diameter of the wafer W. Hence, whilst step-by-step moving the optical assemblies and area sensors from the center region of the wafer towards its periphery region along the X-axis, the half of the wafer located within the inspection area IA is strip-by-strip inspected. At each relative location of the moving elements relative to the wafer, each of the sensors $AS_1$–$AS_5$ acquires an image of the illuminated region $S_1$ and generates data representative thereof. The respective utilities of the control unit 26 receive and analyze these data to locate defects, if any, within the entire illuminated strip S composed of the regions $S_1$–$S_5$.

The illumination assembly 24 operates in a so-called "bright-field illumination" mode. As further shown in FIG. 3b, the scanning apparatus 18 comprises an additional illumination assembly 40 (constituting an additional illumination assembly) mounted inside the housing 22 for the purpose to move together with the optical assemblies $OA_1$–$OA_5$ and sensors $AS_1$–$AS_5$ within the inspection area IA.

FIGS. 4a and 4b illustrate one possible design for the illumination assembly 40. In both examples, the illumination assembly 40 is composed of a corresponding number of light sources, each associated with a corresponding one of the optical assemblies (not shown here). According to the example of FIG. 4a, such a light source is designed like a ring 41 formed by a plurality of LEDs or optical fibers (not shown). In the case of optical fibers, an external light source (not shown) associated with a fiber bundle 42 may be used. The ring 41 would enclose the corresponding field lens (not shown). In the example of FIG. 4b, the light source is designed like a cylinder 43, which also may be formed by a plurality of LEDs. It should, however, be noted that the illumination assembly 40 may include either a single elongated light source mounted in the proximity of the field lenses 34 of the optical assemblies so as to extend along the Y-axis, or a pair of such elongated light sources mounted at opposite sides of the optical assemblies.

Turning now to FIGS. 4c–4f, there is illustrated another possible design of a dark-field illumination assembly 140, aimed at providing the illumination of each region on the wafer at substantially 45°-angle between the vertical plane defined by the average direction of the incident beam propagation and those of the pattern (as seen from the top). This is associated with the fact that a pattern on the wafer is typically arranged in the so-called "streets-and-avenues" manner, and the illumination at 45°-azimuth angle, $\alpha$, enables to eliminate or at least significantly reduce the undesirable diffraction effects caused by the pattern.

As shown in FIG. 4c, the illumination assembly 140 is in the form of a rectangular frame, and comprises a plurality of light sources 142 (e.g., LEDs) and a plurality of identical transparent ball-like lenses 144. It should, however, be noted that generally the lens 144 may be of another suitable shape, being shaped like a ball in the present example. The balls 144 are arranged in rows and columns so as to form four sides of the rectangular frame, such that contact is provided between each two adjacent balls. Each of the light sources is located in the corresponding one of the spaces formed between the balls. The ball 144 has the diameter of about 3 mm, and is made either from glass or optical-quality plastic. The light source 142 is about 0.3 mm in size.

As shown in FIG. 4d, the projecton of a field of view $F_i$ of the corresponding sensor $AS_i$ is located in the center of the horizontal plane defined by the rectangular frame 140 enclosing the field of view $F_i$. The length of the frame's wall is about 1.5-2 times larger than that of the field of view F, of the area sensor.

FIGS. 4e and 4f partly show top and side views, respectively, of the balls-LEDs assembly 140. Each ball 144 serves as a lens accommodated in the optical path of a light beam B emitted by the corresponding LED 142. The light beams B propagate through the corresponding balls 144 and, whilst ensuing therefrom, become directed onto the wafer W at 45°-azimuth angle. To this end, the emitting surface of the LED is appropriately oriented with respect to the corresponding balls, and is located in the focus plane thereof It should be noted that the 45°-angle provided by the LED-balls assembly is the azimuth angle, while an elevation angle, θ, may be different. The term "elevation angle" used herein is the angle between the incident beam and the wafer's plane as seen from the side.

Figure 4G:
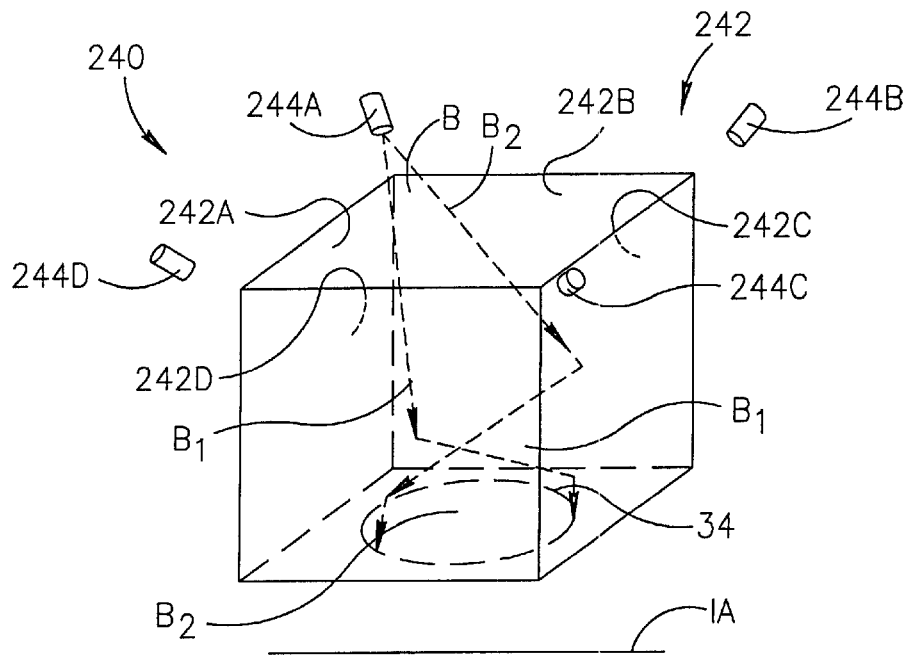
FIGS. 4g and 4h illustrate yet another possible example of a dark-field illumination assembly.
Figure 4H:
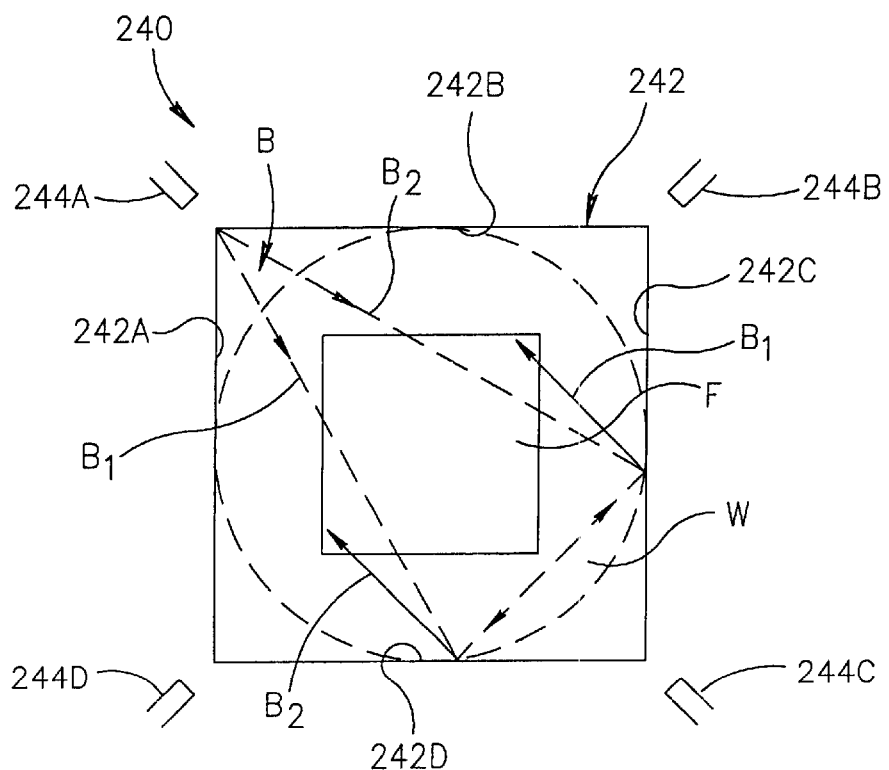

Referring to FIGS. 4g and 4h, there is illustrated yet another possible design of a dark-field illumination assembly, generally designated 240, aimed at providing the illumination with the substantially 45°-angle. This example presents a so-called "retro-reflective scheme". The illumination assembly 240 comprises a rectangular frame 242, and four light sources (e.g., LEDs) 244a, 244b, 244c and 244d which are accommodated at the upper corners of the frame 242, respectively, aimed at providing the propagation of their central beams at the opposite corners. The inner surfaces 242a–242d of the frame 242 are mirrors. The frame 242 is vertically aligned with the corresponding field lens 34. The construction is such that the projection of the field of view F of the corresponding sensor (not shown) occupies the central region of the frame. The light sources 244a–244d are accommodated in the focal plane of the field lens 34. Each light source emits a beam B, which slightly diverges, e.g., within the angle of 14°, and, while propagating towards the lens 34 through the frame 242, is sequentially reflected from two adjacent mirrors located opposite (along the diagonal axis) to the corresponding light source.

As better shown in FIG. 4h, the opposite, periphery light components $B_1$ and $B_2$ of the diverging beam B (solid angle) emitted by the light source 244a impinge vs onto the mirrors 242c and 242d, and being reflected therefrom, fall onto the mirrors 244d and 244c, respectively, which, in turn, reflect the light components $B_2$ and $B_1$ towards the lens 34. As a result, light beams emitted by all the sources and propagating as described above impinge onto the field lens 34 at the substantially near 45°-angle, which lens produces collimated beams of 45°-azimuth angle of incidence. This construction provides the dark-field illumination of an area within the entire field of view F of the area sensor, with the desired uniformity of illumination.

It should be noted that the provision of the illumination assembly operating in the dark-filed illumination mode is optional. Should this assembly be used, its operation is timely separated from the option of the bright-field illumination assembly 24, and it may be operated selectively. In other words, whilst continuously inspecting the wafer using the illumination assembly 24, at selective locations on the wafer (strips), the operation of the assembly 24 is halted and the dark-field illumination assembly is switched-on. These selective locations may be those, where a potential defect has been detected during the bright-field illumination mode of the system 12, or a real defect is expected, which is usually the case when dealing with such patterned workpieces as wafers.

Figure 5A:
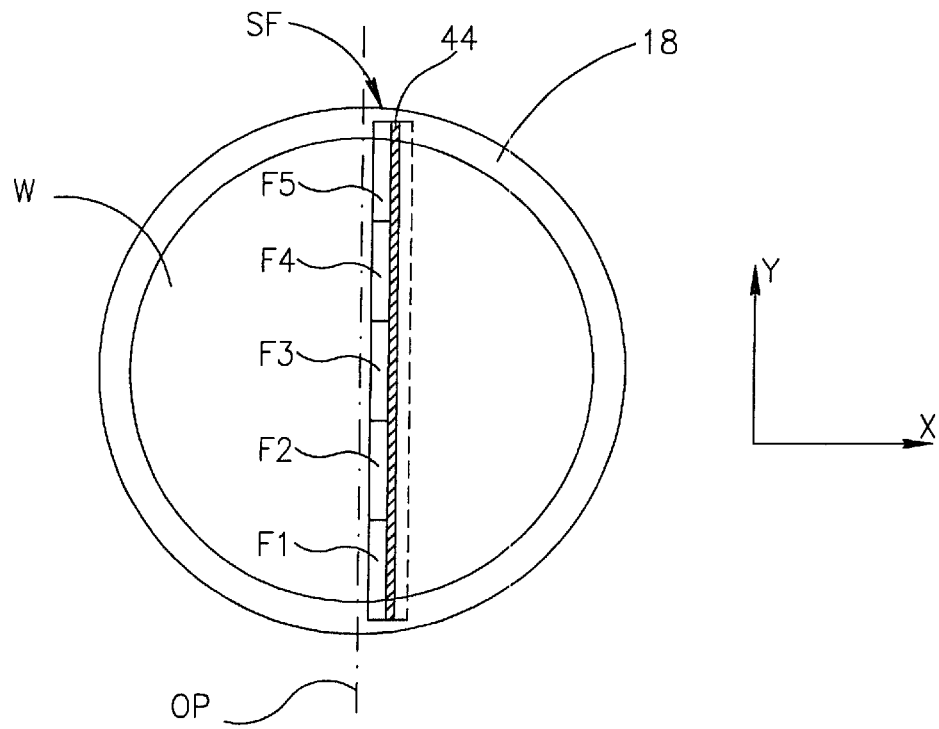
FIGS. 5a and 5b illustrated two different examples, respectively, of a scanning technique suitable to be used in the present invention.
Figure 5B:
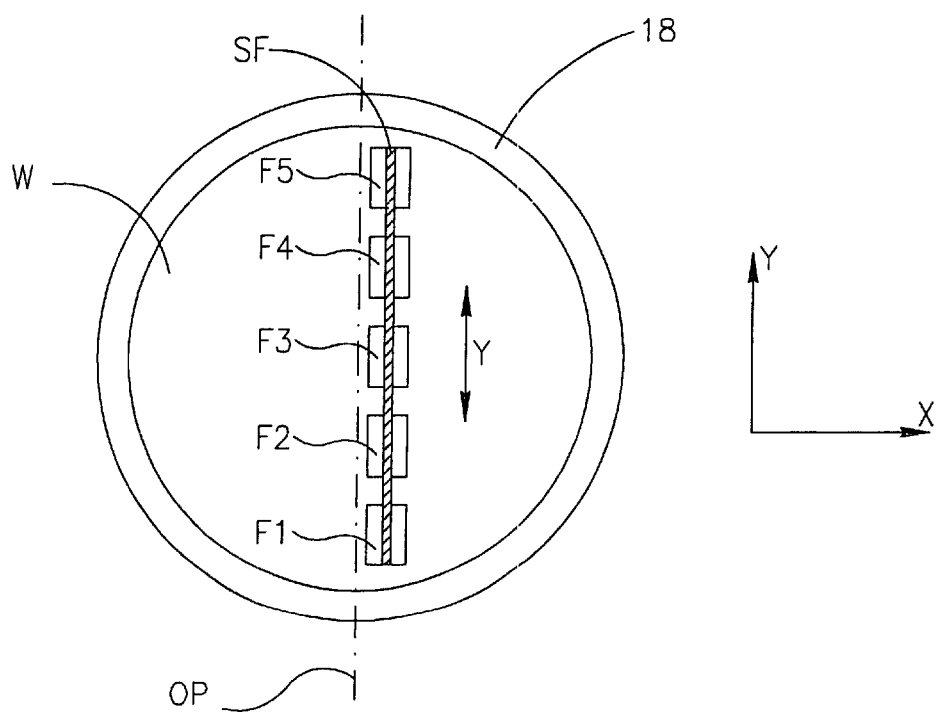

Referring to FIGS. 5a and 5b, there are illustrated two different examples of a scanning technique suitable to be used in the present invention, aimed at inspecting a strip-like scanning field SF on the wafer by all the sensors $AS_1$–$AS_5$. As shown in FIG. 5a, the fields of view $F_1$–$F_5$ of the sensors $AS_1$–$AS_5$ are aligned along the Y-axis and define together a continuous scanning field SF that extends along the wafer's diameter. The movement of the housing 22 along the X-axis is such so as to provide a small overlap region 44 between tile scanning fields of each two locally adjacent positions of the sensors $AS_1$–$AS_5$.

In the example of FIG. 5b, at each current position of the sensors $AS_1$–$AS_5$ along the X-axis, the entire scanning field is formed by the fields of view $F_1$–$F_5$ of all the sensors $AS_1$–$AS_5$. These fields of view cover a corresponding number (five in the present example) spaced-apart areas aligned along the Y-axis; rather than the overlapping areas as in the previously described example In other words, such a scanning field is "discontinuous". This is associated with the fact that the specular reflection from a patterned article, such as wafer, will unavoidably require the field lens to be at least slightly larger maxi the field of view of the area sensor, which creates the spaces between the fields of views of the adjacent sensors. When dealing with the detection of non-spec reflected light (Lambertian), the example of FIG. 5a provides sufficient results. To cover the spaces between the locally adjacent areas, thereby providing the continuous scanning field SF, additional step-like movement of the optics (and, optionally, the corresponding sensors) is provided along the Y-axis, with a pitch not less than the space between the areas (preferably, slightly exceeding this space).

Turning back to FIG. 3a, a so-called "calibration target" is formed along a strip 23 on the window 22a. The calibration target 23 serves for calibrating the sensors prior to inspection, for example, correcting the non-uniformity of illumination, etc.

Figure 6:
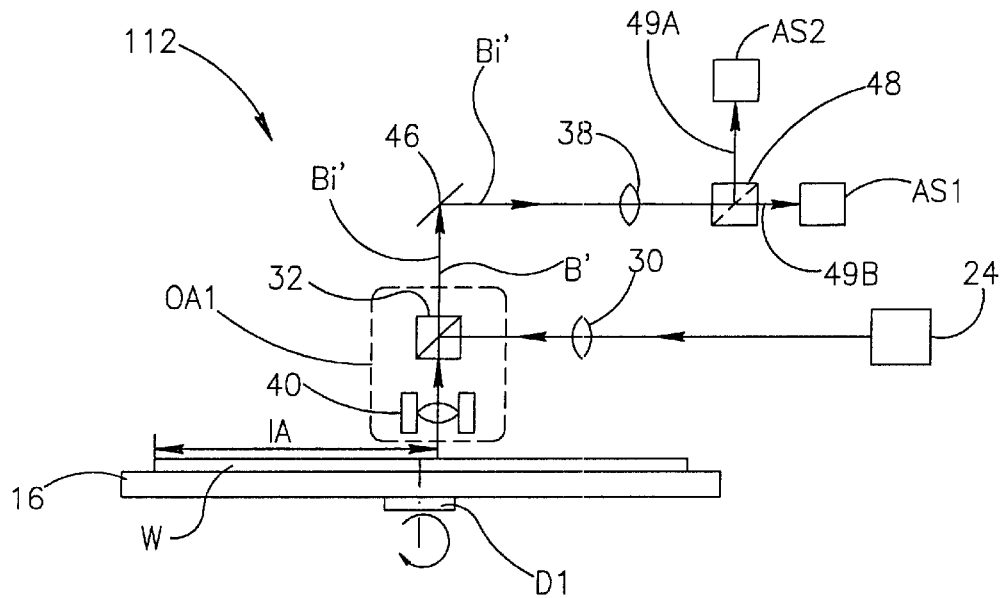
FIG. 6 schematically illustrates the main components of the optical inspection system of either of FIGS. 2 or 3, constructed according to another embodiment of the invention.

Reference is made to FIG. 6, illustrating an optical inspection system 112 constructed according to another embodiment of the invention, suitable to be used in the photolithography arrangement of either of FIGS. 2a or 2b. Similarly, the same reference numbers are used for identifying common components of the systems 12 and 112, and the beam propagation is shown schematically. A scanning apparatus 116 of the system 112 has a somewhat different construction as compared to that of the system 12. Here, the following elements are accommodated inside the housing 22: optical assemblies $OA_1$–$OA_5$, illumination assembly 40, sensors $AS_1$–$AS_5$, a plurality of mirrors 46 (or a single elongated mirror) aligned along the Y-axis above the optical assemblies, imaging tube lenses 38 and an additional light directing assembly. 48. It should be noted, although not specifically shown here, that the drive mechanism $D_2$ is also mounted inside the housing 22 and is coupled to the optical assemblies $OA_1$–$OA_5$ and to the mirror(s) 46 for driving the reciprocation movement thereof Additionally, in the system 112, in distinction to the previously described embodiment, the sensors $AS_1$–$AS_5$ are stationary mounted inside the housing 22, rather than being mounted for movement together with the optical assemblies $OA_1$–$OA_5$. The additional light directing assembly 48 serves for dividing the returned light components $B_i'$ reflected from the mirror 46 into two groups 49a and 49b propagating, respectively, along the Z- and X-axes.

Figure 7:
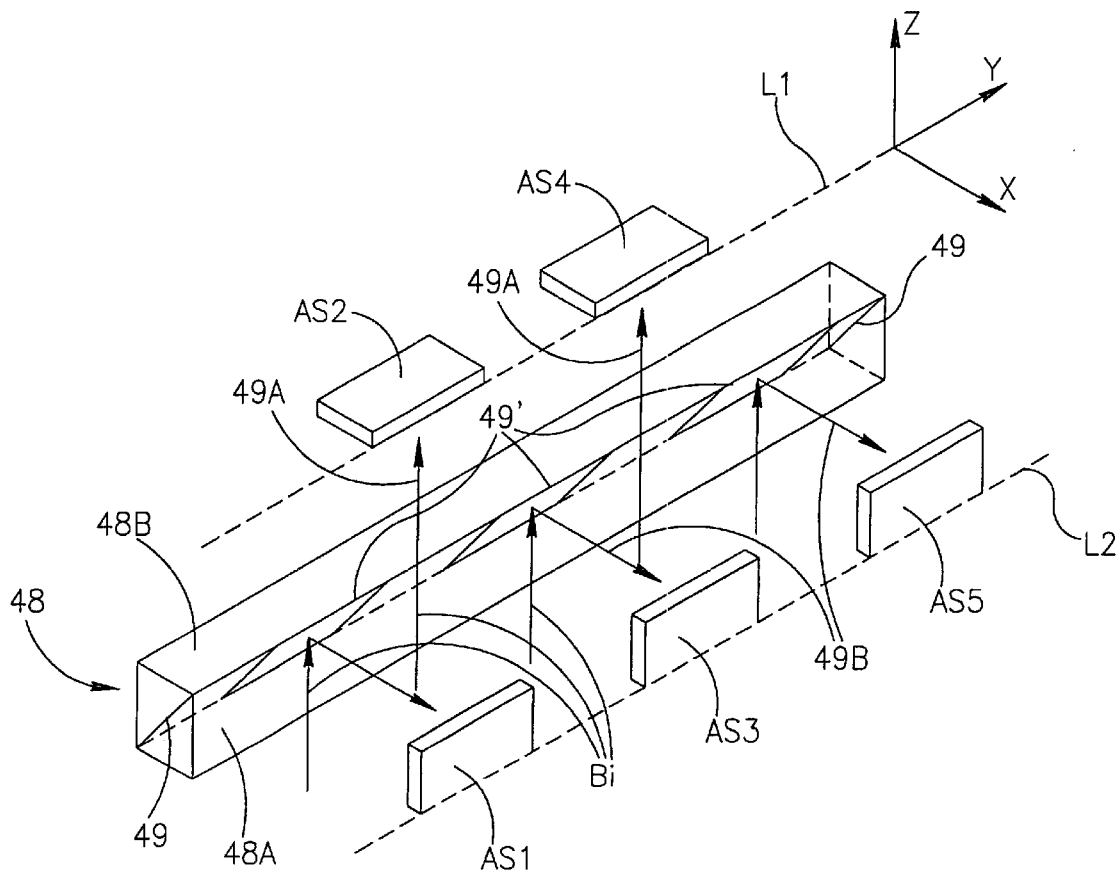
FIG. 7 more specifically illustrates an arrangement of sensors of the system of FIG. 6.

As shown in FIG. 7, the sensors $AS_1$–$AS_5$ are aligned in two parallel lines $L_1$ and $L_2$ which extend along the Y-axis and are spaced from each along the X- and Z-axes. Each two adjacent sensors are spaced from each other along the X- and Z-axes. The light directing assembly 48 is in the form of a parallelepiped, which is substantially optically transparent, except for spaced-apart reflective regions 49b formed on its inner diagonal surface 49.

Figure 8A:
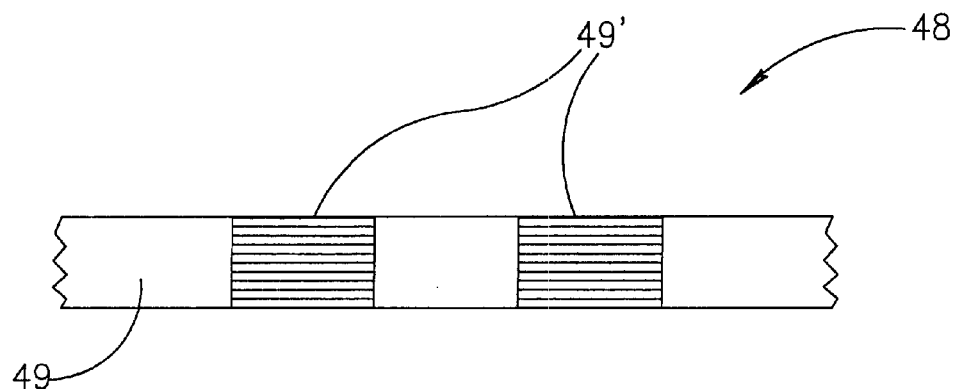
FIGS. 8a and 8b more specifically illustrate a light directing assembly of the system of FIG. 6.
Figure 8B:
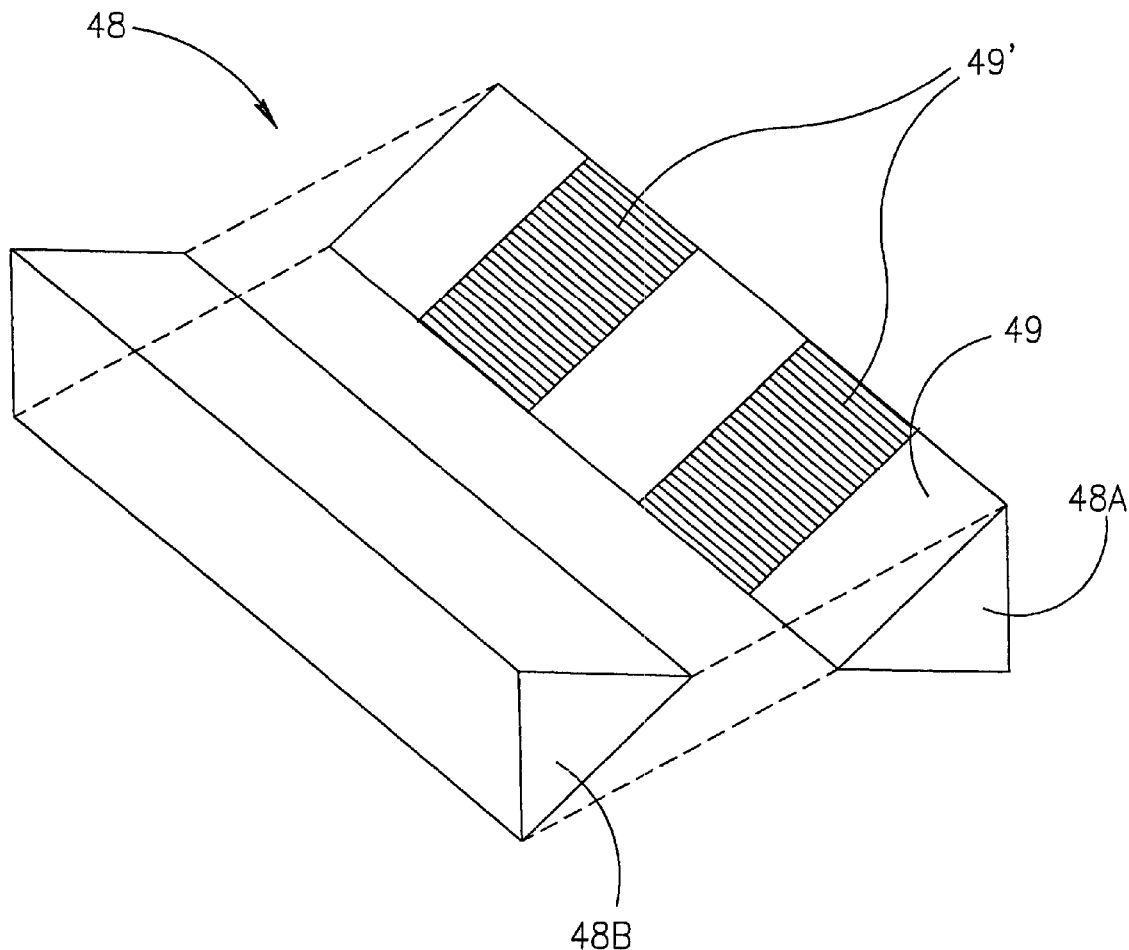

As shown in FIGS. 8a and 8b, the light directing assembly 48 may be constructed by attaching a pair of parallel sides of a pair of symmetrically identical triangular prisms 48a and 48b to each other. One of these parallel sides has the patterned surface 49. The pattern may, for example, be made by depositing a reflective material onto the regions 49a through a mask. It should be noted, although not specifically shown, that beam-splitter cubes may replace the prisms 48a and 48b.

The operation of the system 112 is generally similar to that of the system 12. The moving elements (i.e., the optical elements $OA_1$–$OA_5$, mirror(s) 46, and, optionally, the illumination assembly 40) step-by-step move along the X-axis between the center region and the periphery region of the wafer (i.e., within the inspection area IA). One half of the wafer is strip-by-strip inspected. Then, the stage 16 rotates by 180° parallel to the inspection plane IP, resulting in tat the other half of the wafer is positioned within the inspection area IA, and the inspection is repeated by step-by-step moving the respective elements from the periphery region of the wafer towards its center region.

It is understood that the moving elements may be returned to their initial position above the center region of the wafer prior to starting the inspection of the second half of the wafer. Thus, the inspection proceeds from the center region to the periphery region of the wafer.

With regard to the example of FIG. 5b, it should be understood that various operational modes are possible. For example, after completing the scanning of the half of the wafer by step-by-step movements along the X-axis, the fields of view of the sensors are shifted along the Y-axis and the inspection area IA is passed with this shifted position of the fields of view. In this case, the sensors may and may not be returned into their initial position relative to the wafer prior to the shifting procedure. An alternative operational mode consists of step-by-step performing the Y-axis shift of the fields of view for each sensors' position along the X-axis.

It should be noted that, generally, the number of area sensors, and, accordingly, of the optical assemblies, suitable to be used in the system 12, 112 is dictated by the dimensions of the wafer to be inspected and the desired image resolution. For example, if a standard 200 mm wafer should be inspected with the resolution of 50 μm, eight commercially available TV cameras (i.e., each having approximately 500×600 pixels) may be used as the area sensors. In this case, since these cameras operate with the frequency of 60 frames per second, the scanning time at each relative location of the moving components relative to the wafer (i.e., for each illuminated strip) is approximately 170 msec, the time for moving these elements from strip to strip is about 0.5 sec, the inspection area (one half of the wafer) includes four illuminated strips (considering the overlap regions), and the total inspection time for the entire wafer is about 5.4 sec. Taking into consideration the time required for such additional operations as loading/unloading of the wafer, rotation of the stage, calibration, etc., total inspection time per wafer would be about 10 sec. It is understood that such brief inspection time would not affect the throughput of the photolithography arrangement, nor would it impede the regular operation of the robot.

Figure 9A:
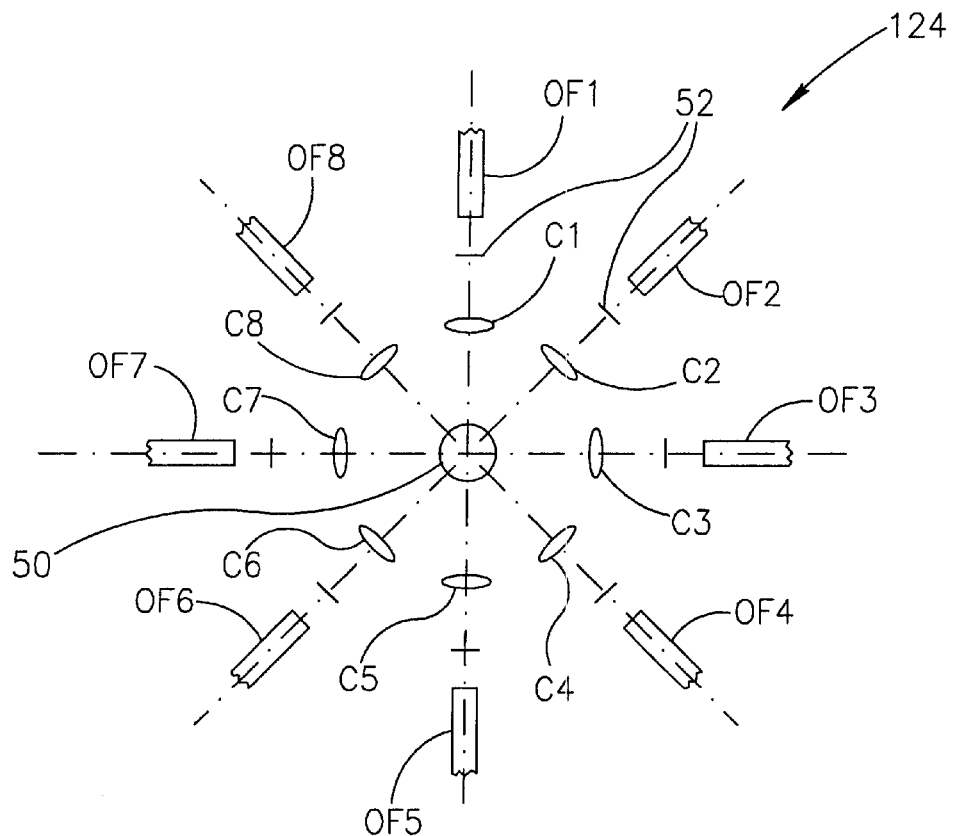
FIGS. 9a and 9b illustrate two different examples, respectively, of the illumination assembly suitable for use in the system of either of FIGS. 3a–3b or 6.
Figure 9B:
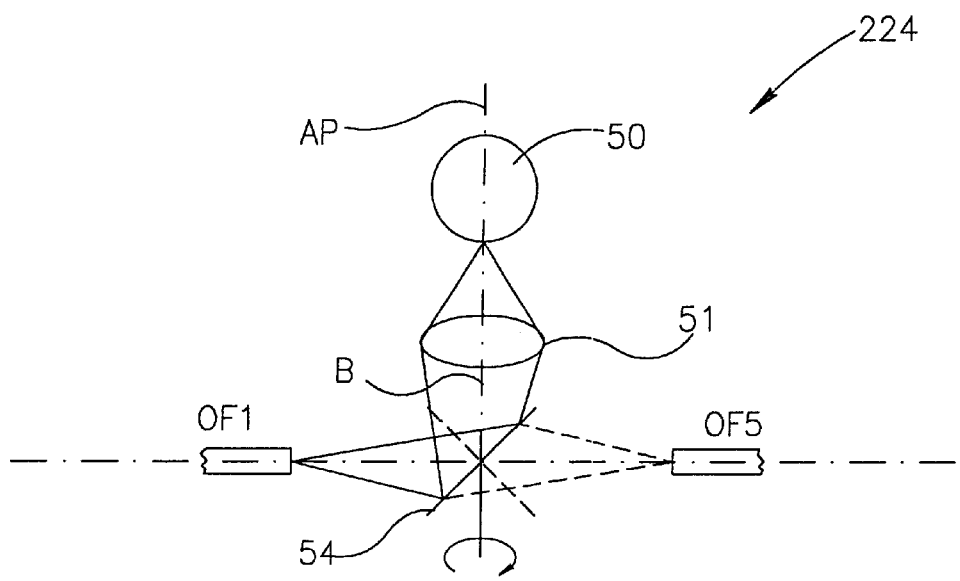

According to the present invention, a large area of the wafer (i.e., a strip extending along the entire diameter of the wafer) should be illuminated at each relative location of the optical assemblies relative to the wafer W. As indicated above, the illumination assembly may comprise a suitable number of light sources. However, to avoid the requirement for significantly high illumination energy, and also to prevent overlapping between the neighboring illuminated areas which produces undesirable non-uniformity of the illumination, a single light source equipped with suitable light splitting means capable of producing a plurality of incident light components may be provided. FIGS. 9a and 9b illustrate two possible constructions of such an illumination assembly having a single light source.

In the example of FIG. 9a, an illumination assembly 124 comprises a lamp 50 associated with a plurality of condensers $C_1$–$C_5$ and optical fibers $OF_1$–$OF_8$, eight in the present example, considering eight cameras and eight optical assemblies. Eight shutters, generally at 52, are provided, each associated with a corresponding one of the optical fibers. The shutters may be of either mechanical or electrooptical type.

The provision of the shutters 52 is aimed at the following. Whilst illuminating the plurality of regions within the illuminated strip S trough separate field lenses 34, a certain overlap of two locally adjacent illuminated regions occurs, unavoidably resulting in the non-uniform illumination within such an overlapping area. To avoid this effect the array of the regions within the strip S may be illuminated sequentially, by sequentially opening the shutters 52. Alternatively, the shutters may be operated in such a manner that the regions illuminated at each time unit are disposed in a so-called "chess-board" order, thereby enabling the interlaced illumination. It should be noted that such shutters enabling the sequential illumination of the array of regions within the strip or the interlaced illumination of these regions may also be used with a plurality of separate light sources.

FIG. 9b illustrates a section view of an illumination assembly 224 having a somewhat different construction as compared to the assembly 124. The assembly 224, similarly to the assembly 124, includes the lamp 50, a condenser 51 and a plurality of optical fibers (fibers $OF_1$ and $OF_5$ are shown in the figure), but is also provided with a mirror 54 The mirror 54 is mounted in the optical path of a primary beam B, and is rotatable, preferably step-by-step, about an axis AP of propagation of the beam B towards the mirror 54, by a suitable driver (not shown). In other words, the mirror 54 is oriented at 45° to the vertical axis AP, and rotates in the horizontal plane, the input faces of the optical fibers being arranged in a spaced-apart relationship in the horizontal plane. Thus, the rotation of the mirror 54 will result in the sequential illumination of the input faces of the optical fibers and, consequently, the regions within the strip S. For example, when using ten conventional TV cameras, with the scanning time per one strip being about 128 μs, the frequency of the rotation of the mirror 54 is about 7 Hz. The synchronization of the rotation of the mirror 54 from one fiber to the adjacent fiber, as well as the synchronization of the shutter's operation, are controlled either by the programming means of the control unit 26 or by optical sensors appropriately provided.

It should also be noted that, when dealing with a circular workpiece (e.g., wafer), only the inspection of the central strip extending along the diameter of the workpiece, needs the entire set of cameras to be operated for inspection. Thus, for saving the overall inspection time, whilst inspecting periphery strips of the circular workpiece, only some of the cameras (i.e., centrally located within the array of the cameras) may actually be engaged in the inspection process. An additional synchronization utility of the control unit 26 may operate for preventing imaging by the periphery detection channels.

Figure 10:
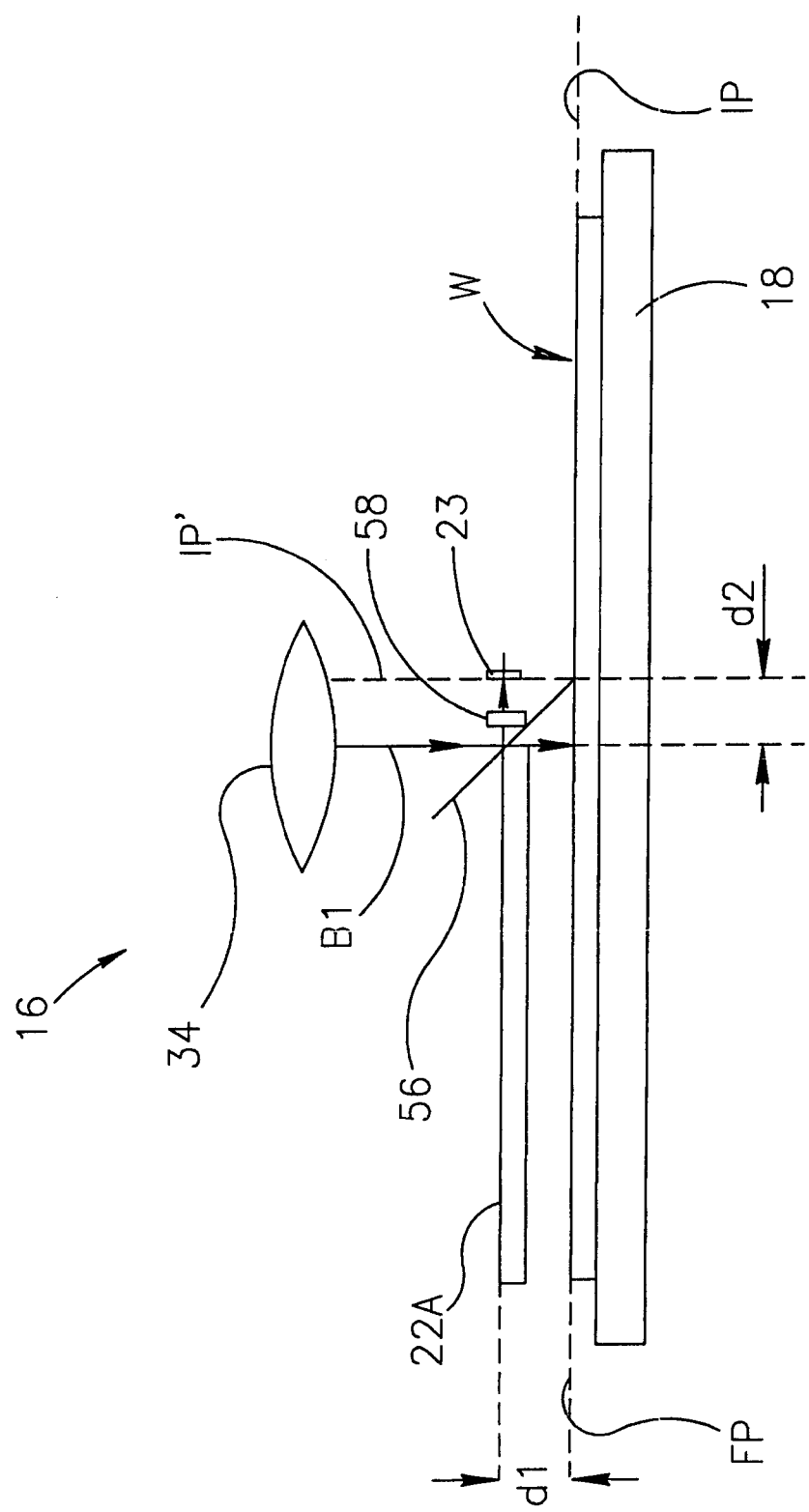
FIG. 10 illustrates more specifically some features of the scanning apparatus of FIGS. 3a–3b.

One more feature of the present invention will now be explained with reference to FIG. 10, which partly illustrates the scanning apparatus 18. It is understood that the wafer W under inspection is located in a focal plane FP of the objective lens assemblies (shown here as field lenses 34). As indicated above, the calibration pattern 23 is provided serving for calibrating the sensors prior to inspection, and should therefore be also located in the focal plane FP. For this purpose, the calibration pattern 23 extends parallel to the inspection plane IP but is located in a plane IP' perpendicular thereto, and a mirror 56 is accommodated in the optical path of the incident beam ensuing from the field lens 34. The location of the mirror is selected such as to ensure that the optical distance d1 between the optical window 22A and the wafer (i.e., the focal plane FP) is equal to the distance $d_2$ between the plane IP' and a point 56A of incidence of the beam $B_1$ onto the mirror 56. The mirror 56 is mounted stationary, and therefore does not impede the inspection of the half of the wafer through the moving optical assemblies. As shown in FIG. 10, a glass-piece 58 is preferably accommodated in the optical path of the incident beam $B_1$ on its way towards the calibration pattern 23. This enables to obtain substantially identical conditions for light propagation during the inspection and calibration procedures.

The advantages of the present invention are self-evident. The optical inspection system constructed and operated according to the invention, is compact, provides for maintaining the wafer stationary during the inspection and utilizes a rigid and very stable scanning apparatus capable of fist scanning of the wafer. The scanning apparatus is fully separated from the photolithography environment, owing to the fact that all moving components of the scanning apparatus are located within the sealed housing 22, while the control unit 26 and illumination assembly 24 are located outside the track clean area. As indicated above, the optical inspection system according to the invention has the option to be bypassed by the production process and to be simultaneously operated in off-line or integrated modes.

It will be appreciated by persons skilled in the aft that the present invention is not limited to the control of the photolithography process applied to silicon-based wafers. Rather, any of the embodiments described hereinbefore and any modifications thereof may be employed, for example, for controlling the etching process, CVD, etc. Various modifications and changes may be applied to the preferred embodiments of the invention as hereinbefore exemplified without departing from its scope as defined in and by the appended clears.

What is claimed is:

1. An optical inspection system for detecting defects on a substantially flat workpiece having an axis of symmetry, the system comprising a stage supporting said workpiece in an inspection plane, and a scanning apparatus accommodated above said workpiece, wherein:
    (a) said stage is mounted for rotation in a plane parallel to said inspection plane;
    (b) said scanning apparatus is constructed to define an inspection area covering substantially a half of the workpiece, thereby enabling half-by-half inspection of the workpiece, and comprises:
        an illumination assembly producing a plurality of incident radiation components, each component illuminating a corresponding one of a plurality of regions of the workpiece within a strip illuminated by said plurality of incident radiation components, the strip extending parallel to the axis of symmetry of the workpiece between two opposite sides thereof;
        a plurality of optical assemblies accommodated above said workpiece, each optical assembly directing a corresponding one of a plurality of radiation components returned from the corresponding illuminated region away from the workpiece, wherein the optical assemblies are aligned along said axis of symmetry in a spaced-apart parallel relationship, and are mounted for reciprocating movement within a plane parallel to the inspection area covering substantially half of the workpiece;
    (c) a plurality of area sensors are arranged in a predetermined manner, each area sensor being associated with a corresponding one of the optical assemblies for receiving the component of the returned radiation and generating data representative thereof;
    (d) a first drive mechanism is coupled to said optical assemblies for driving said reciprocating movement thereof; and
    (e) a second drive mechanism is coupled to said stage for driving said rotation thereof.

2. The system according to claim 1, wherein said illumination assembly operates in a bright-field illumination mode.

3. The system according to claim 2, and also comprising an additional illumination assembly producing additional incident radiation and operating in a dark-field illumination mode.

4. The system according to claim 3, wherein said additional illumination assembly is mounted for the reciprocating movement together with the optical assemblies.

5. The system according to claim 3, wherein said additional illumination assembly extends along said axis of symmetry.

6. The system according to claim 3, wherein said additional illumination assembly comprises a plurality of light sources, each associated with a corresponding one of the optical assemblies.

7. The system according to claim 6, wherein each of the light sources is associated with at least one corresponding light directing assembly, so as to provide a substantially 45°-angle of incidence of the light component emitted by the light source onto the workpiece.

8. The system according to claim 7, wherein the light directing assembly is in the form of a plurality of rectangular frames, each frame corresponding to one of the area sensors, the projection of the field of view of said area sensor occupying a central region of a horizontal frame defined by said frame.

9. The system according to claim 8, wherein each side of said frame is formed by a two-dimensional matrix of substantially small lenses, contact being provided between each two adjacent lenses, each of said light sources being located within a corresponding one of spaces between the lenses.

10. The system according to claim 8, wherein
    each of said frames is accommodated above a field lens of the corresponding one of the optical assemblies;
    inner sides of said frame are mirrors; and
    the four light sources are accommodated at the upper comers of the frame so as to be in a focal plane of the corresponding field lens, in the corresponding optical assembly.

11. The system according to claim 1, wherein said plurality of optical assemblies are mounted for the reciprocating movement along an axis perpendicular to the axis of symmetry, overlapping being provided between fields of view of each two adjacent area sensors.

12. The system according to claim 11, wherein said plurality of optical assemblies are mounted for the reciprocating movement along an axis parallel to the axis of symmetry, the field of views of the plurality of area sensors being aligned in a spaced-apart relationship along an axis parallel to the axis of symmetry.

13. The system according to claim 12, wherein the light source is a lamp, and the guiding means are optical fibers.

14. The system according to claim 1, wherein said illumination assembly comprises a plurality of light sources producing said components of the incident is radiation and directing each of said components onto a corresponding one of the optical assemblies.

15. The system according to claim 1, wherein said illumination assembly comprises a single light source producing a plurality of light components, and a plurality of light guiding means, each receiving a corresponding one of the light components and directing it towards the corresponding optical assembly.

16. The system according to claim 1, wherein said illumination assembly comprises a single light source producing a light component, a plurality of light guiding means, and a light directing element for sequentially directing the light component to a corresponding one of the light guiding means.

17. The system according to claim 16, wherein said light source is a lamp, said guiding means are optical fibers, and said light directing means is a rotatable mirror.

18. The system according to claim 1, wherein each of said optical assemblies comprises a field lens and a beam splitter.

19. The system according to claim 1, wherein each of the area sensors is an area CCD.

20. The system according to claim 1, wherein said area sensors are arranged in a line parallel to said axis of symmetry, and are associated with the optical assemblies for the reciprocating movement together with the optical assemblies.

21. The system according to claim 1, wherein said area sensors are arranged in two parallel lines parallel to the axis of symmetry, such that each two adjacent sensors are spaced from each other along two mutually perpendicular axes, a light directing means being provided for receiving the components of the returned radiation ensuing from the optical assemblies and directing them onto the area sensors.

22. A photolithography arrangement for processing a stream of substantially flat workpieces progressing on a production line, the tool comprising inter alia an optical inspection system for detecting defects on the workpiece of a kind having an axis of symmetry, the system comprising a stage supporting said workpiece in an inspection plane, and a scanning apparatus accommodated above said workpiece, wherein:

said stage is mounted for rotation in a plane parallel to said inspection plane;

said scanning apparatus is constructed to define an inspection area covering substantially a half of the workpiece, thereby enabling half-by-half inspection of the workpiece, the scanning apparatus comprising:

an illumination assembly producing a plurality of incident radiation components, each component illuminating a corresponding one of a plurality of regions of the workpiece within a strip illuminated by said plurality of incident radiation components, the strip extending parallel to the axis of symmetry of the workpiece between two opposite sides thereof;

a plurality of optical assemblies accommodated above said workpiece, each optical assembly directing a corresponding one of a plurality of radiation components returned from the corresponding illuminated region away from the workpiece, wherein the optical assemblies are aligned along said axis of symmetry in a spaced-apart parallel relationship, and are mounted for reciprocating movement within the inspection area along axes perpendicular to said axis of symmetry, said inspection area covering substantially half of the workpiece;

a plurality of area sensors arranged in a predetermined manner, each area sensor being associated with a corresponding one of the optical assemblies for receiving the component of the returned radiation and generating data representative thereof;

a first drive mechanism coupled to said optical assemblies for driving said reciprocating movement thereof; and a second drive mechanism coupled to said stage for driving said rotation thereof.

23. A method for inspecting a substantially flat workpiece having an axis of symmetry, the method providing half-by-half inspection of the workpiece and comprising the steps of:

(i) locating the workpiece within an inspection plane;

(j) illuminating a plurality of regions of the workpiece by a plurality of incident radiation components and producing a plurality of light components returned from the plurality of illuminated regions, the illuminated regions forming an illuminated strip extending parallel to the axis of symmetry between two opposite sides of the workpiece;

(k) directing each of the plurality of light components returned from the illuminated regions through a plurality of optical assemblies aligned in a line parallel to the axis of symmetry above the workpiece;

(l) detecting light components returned from the illuminated regions by a corresponding plurality of area sensors;

(m) moving said plurality of optical assemblies relative to said workpiece within a plane parallel to the inspection plane, such as to illuminate successive strips on the workpiece and detect light components returned therefrom;

(n) repeating steps (j) to (n) for strip-by-strip inspection of the workpiece within an inspection area that covers substantially a first half of the workpiece;

(o) rotating said workpiece by 180° and repeating steps (j) to (o), thereby inspecting the other half of the workpiece.

24. The method according to claim 23, wherein said step (j) comprises sequential illumination of the plurality of the regions.

25. The method according to claim 23, wherein said step (j) comprises selective illumination of some of said plurality of regions.

26. The method according to claim 25, wherein said selective illumination is such as to prevent overlapping of two simultaneously illuminated regions.

27. The method according to claim 23, wherein said moving comprises providing a reciprocating movement of the plurality of optical assemblies along an axis perpendicular to the axis of symmetry, overlapping being provided between fields of view of each two adjacent area sensors.

28. The method according to claim 27, wherein said moving comprises providing a reciprocating movement of the plurality of optical assemblies along an axis parallel to the axis of symmetry, the fields of view of the area sensors being aligned in a spaced-apart parallel relationship along an axis parallel to the axis of symmetry.

* * * * *

UNITED STATES PATENT AND TRADEMARK OFFICE
CERTIFICATE OF CORRECTION

PATENT NO. : 6,407,809 B1
DATED : June 18, 2002
INVENTOR(S) : Finarov et al.

It is certified that error appears in the above-identified patent and that said Letters Patent is hereby corrected as shown below:

Column 15,
Line 9, after "incident" delete "is".

Signed and Sealed this

Twenty-fourth Day of August, 2004

JON W. DUDAS
*Director of the United States Patent and Trademark Office*